(12) United States Patent
Omoto

(10) Patent No.: US 8,876,703 B2
(45) Date of Patent: Nov. 4, 2014

(54) ROTARY SELF-PROPELLED ENDOSCOPE

(75) Inventor: Keijiro Omoto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1423 days.

(21) Appl. No.: 12/360,390

(22) Filed: Jan. 27, 2009

(65) Prior Publication Data

US 2009/0209812 A1 Aug. 20, 2009

(30) Foreign Application Priority Data

Feb. 15, 2008 (JP) ................................ 2008-034994

(51) Int. Cl.
*A61B 1/00* (2006.01)
*A61B 1/31* (2006.01)
*A61B 1/04* (2006.01)
*A61B 1/05* (2006.01)

(52) U.S. Cl.
CPC ... *A61B 1/31* (2013.01); *A61B 1/05* (2013.01); *A61B 1/00156* (2013.01); *A61B 1/00094* (2013.01); *A61B 1/00158* (2013.01)
USPC ............................ 600/137; 600/104; 600/114

(58) Field of Classification Search
CPC ........... A61B 1/00075; A61B 1/00073; A61B 1/00133; A61B 1/00156; A61B 1/0016

USPC .................................. 600/137, 109, 114, 104
See application file for complete search history.

(56) References Cited

U.S. PATENT DOCUMENTS

| | | | |
|---|---|---|---|
| 6,464,631 B1* | 10/2002 | Girke et al. | 600/109 |
| 7,048,717 B1* | 5/2006 | Frassica | 604/165.04 |
| 7,955,252 B2* | 6/2011 | Suzuki et al. | 600/106 |
| 2005/0222495 A1* | 10/2005 | Okada et al. | 600/114 |
| 2005/0272976 A1* | 12/2005 | Tanaka et al. | 600/114 |

FOREIGN PATENT DOCUMENTS

| | | |
|---|---|---|
| JP | 2003-005093 A | 1/2003 |
| JP | 2006-312017 | 11/2006 |
| JP | 2007-185383 | 7/2007 |
| JP | 2007-313225 A | 12/2007 |

* cited by examiner

*Primary Examiner* — Alireza Nia

(74) *Attorney, Agent, or Firm* — Scully, Scott, Murphy & Presser, P.C.

(57) ABSTRACT

A rotary self-propelled endoscope, including: a tubular outer shaft having an elongated insertion section main body with a distal end portion which is rotatable around a longitudinal axis and has at least partially a surface formed to have a helical configuration; an inner shaft which is rotatably inserted through the outer shaft and is coupled to the distal end portion of the insertion section main body; and a motor unit which causes the inner shaft to rotate around the longitudinal axis from the proximal end side.

7 Claims, 12 Drawing Sheets

ROTARY SELF-PROPELLED ENDOSCOPE

CROSS REFERENCE TO RELATED APPLICATION

This application claims the benefit of Japanese Application No. 2008-034994 filed in Japan on Feb. 15, 2008, the contents of which are incorporated herein by this reference.

BACKGROUND OF THE INVENTION

1. Field of the Invention

The present invention relates to a rotary self-propelled endoscope which propels itself by turning its rotary cylindrical body having a helical structure on the outer peripheral surface thereof.

2. Description of the Related Art

Endoscopes are widely used in medical and other fields for observation of a region such as an inside of a luminal cavity on which no visual inspection can be directly performed. An endoscope is provided with an elongated insertion section, which has been inserted into a subject by a skilled operator.

On the other hand, recently, endoscopes which are inserted using its propulsion for an easier insertion into a luminal cavity have been proposed.

For example, Japanese Patent Application Laid-Open Publication No. 2006-312017 discloses an endoscope system which is configured to have an insertion section and a propulsion generation section for rotating around its axis on an outer peripheral surface of the insertion section, and the propulsion generation section is rotated by a rotational device so that the endoscope system is inserted into a luminal cavity by its own propulsion.

Also, Japanese Patent Application Laid-Open Publication No. 2007-185383 discloses a rotary self-propelled endoscope which is configured to have an insertion section and a rotary cylindrical body having a helically shaped portion for turning around its axis on an outer peripheral surface of the insertion section, and the rotary cylindrical body is rotated by a rotational device so that the endoscope is automatically inserted into a luminal cavity.

SUMMARY OF THE INVENTION

A rotary self-propelled endoscope of the present invention includes: a tubular and elongated insertion section with a distal end portion which is rotatable around a longitudinal axis and has at least partially a surface formed to have a helical configuration; a torque transmitting member which is rotatably inserted through the insertion section and is coupled to the distal end portion of the insertion section; and a drive section which causes the torque transmitting member to rotate around the longitudinal axis.

DETAILED DESCRIPTION OF THE PREFERRED EMBODIMENTS

Now, in conjunction with the drawings, embodiments of the present invention will be explained below.

One Embodiment

Figure 1:
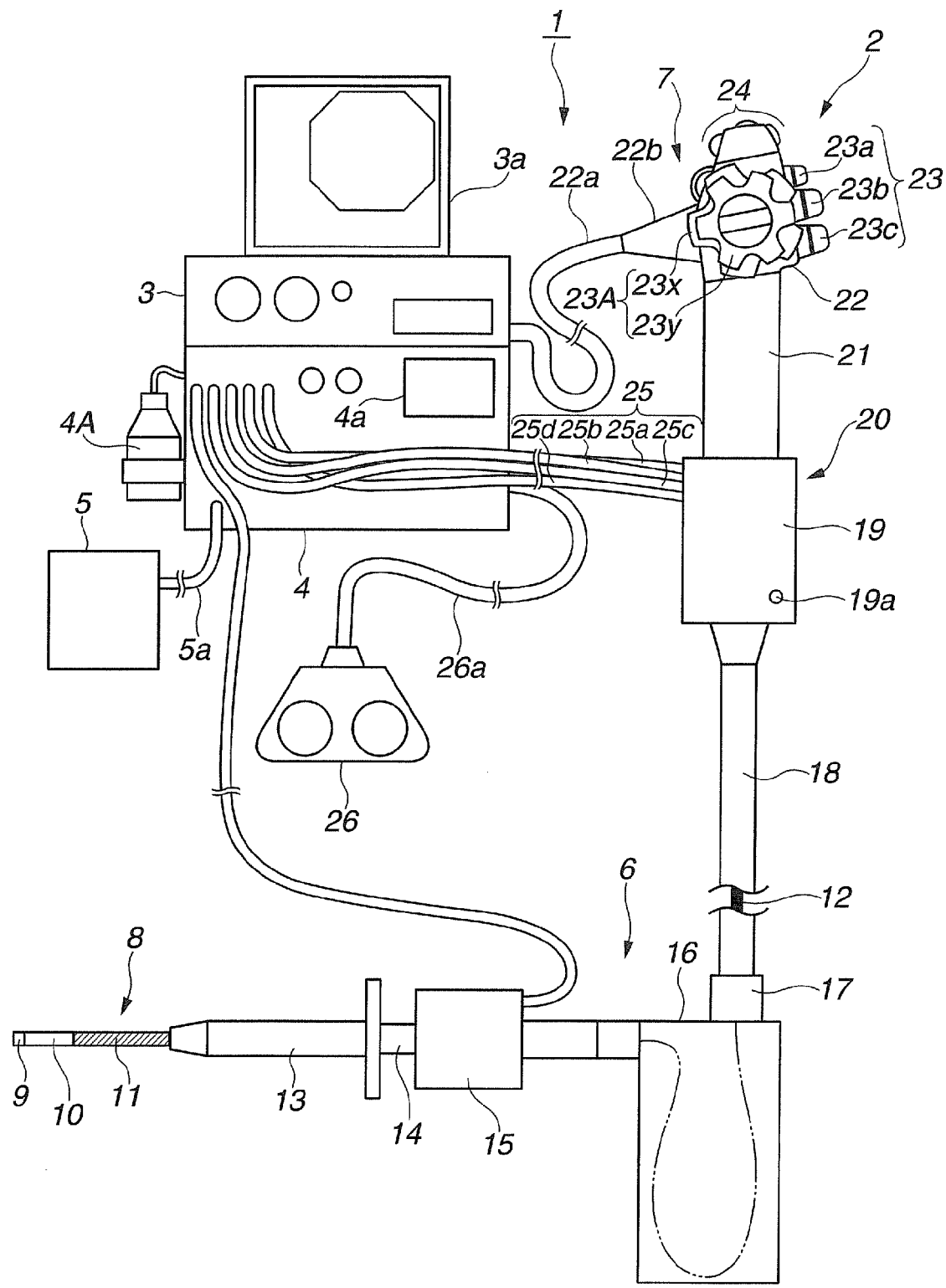
FIG. 1 is an appearance perspective view showing an entire configuration of an endoscope system having a rotary self-propelled endoscope of one embodiment.
Figure 2:
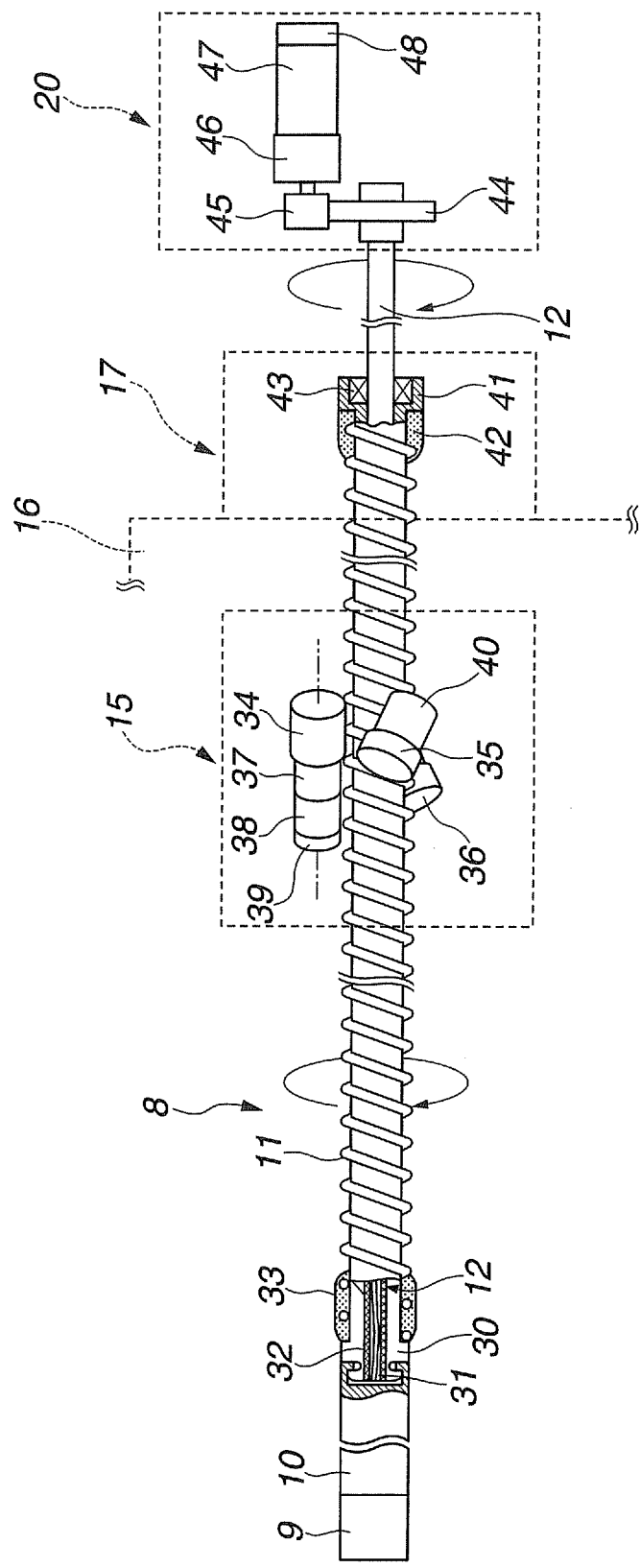
FIG. 2 is a configuration view illustrating a configuration of main sections and an insertion section of the rotary self-propelled endoscope of the embodiment.
Figure 3:
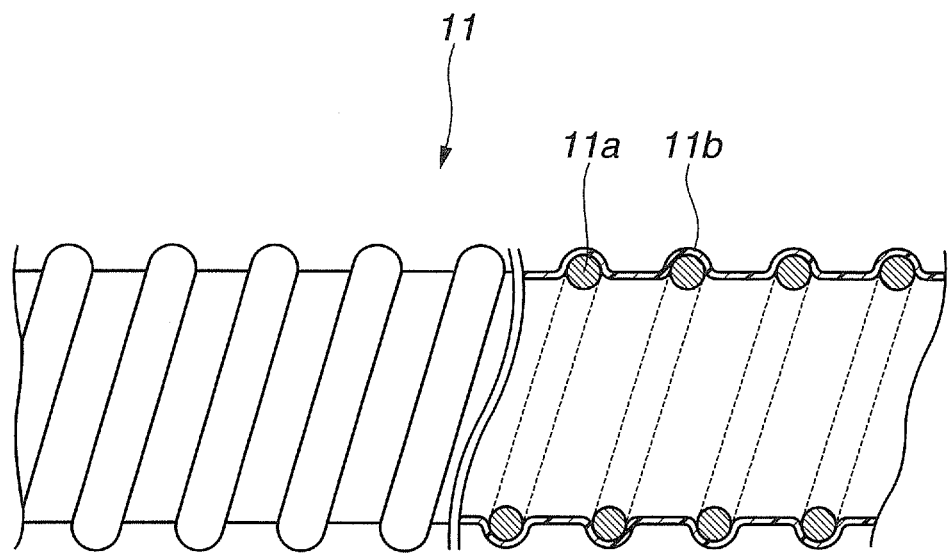
FIG. 3 is a main part enlarged view showing an outer shaft having a helical configuration of the insertion section of the rotary self-propelled endoscope of the embodiment, with a part thereof shown in cross-section.
Figure 4:
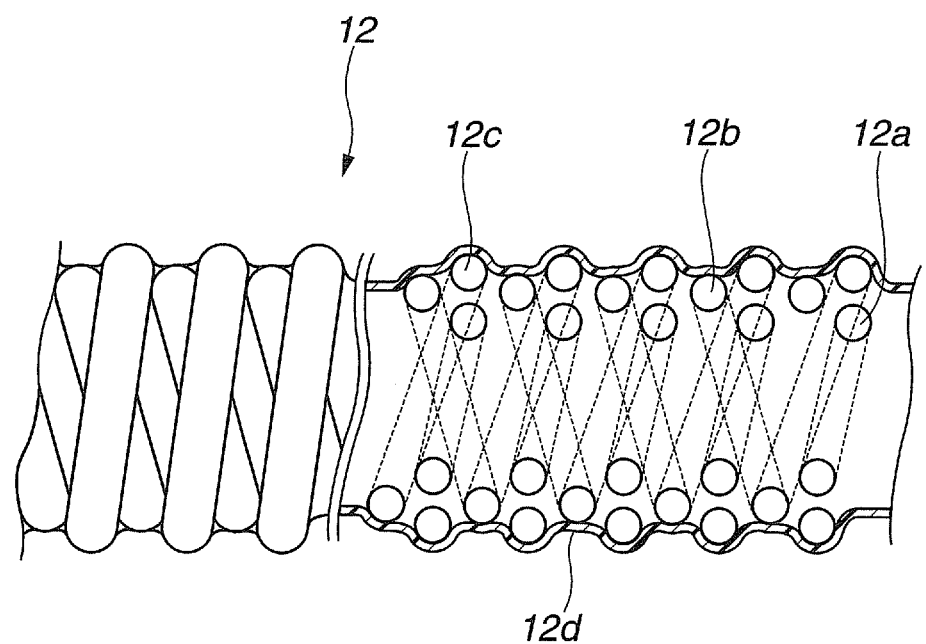
FIG. 4 is a main part enlarged view showing an inner shaft which is wired in the outer shaft of the insertion section of the rotary self-propelled endoscope of the embodiment, with a part thereof shown in cross-section.
Figure 5:
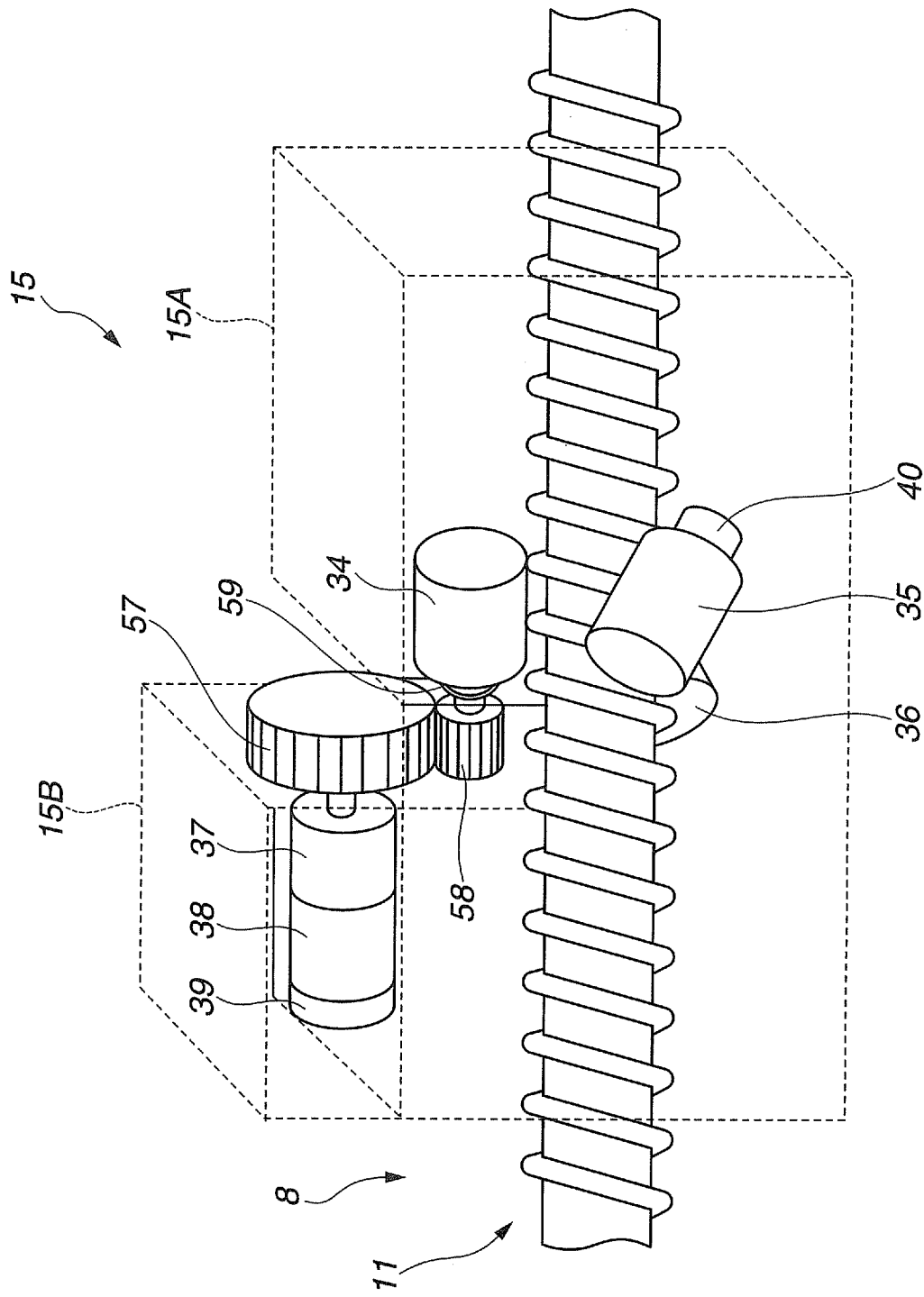
FIG. 5 is a configuration view showing a configuration of an external drive section of the rotary self-propelled endoscope of the embodiment.
Figure 6:
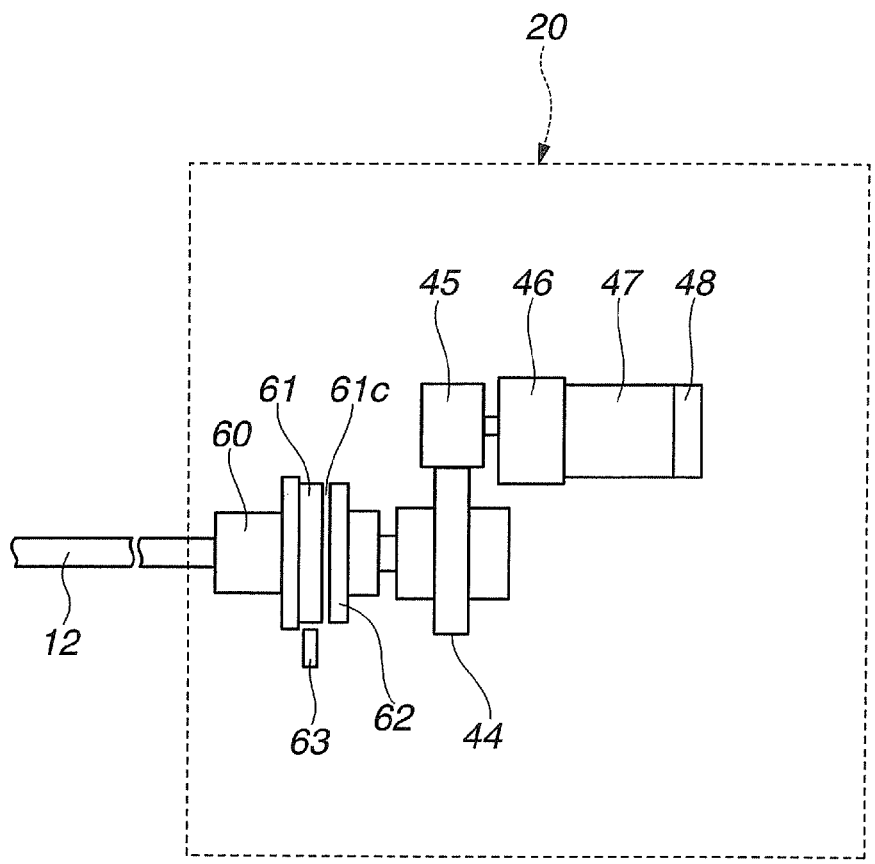
FIG. 6 is a configuration view showing a configuration of a motor box in an operation section of the rotary self-propelled endoscope of the embodiment.
Figure 7:
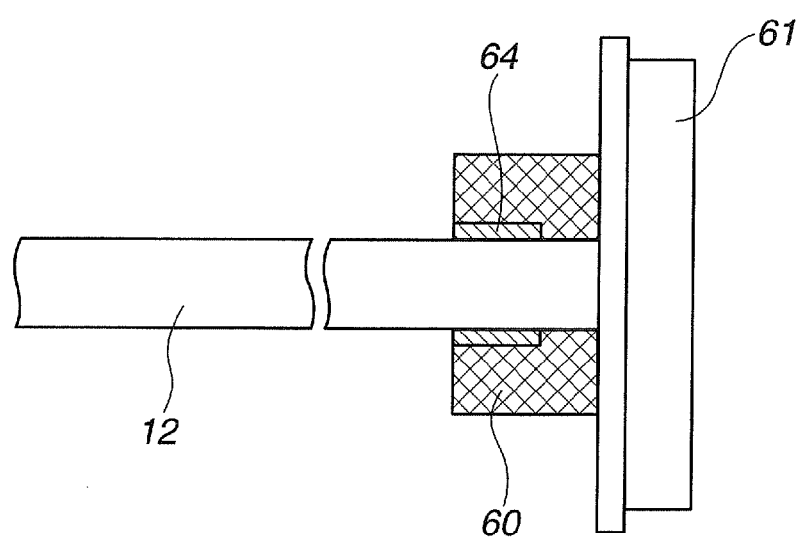
FIG. 7 is a configuration view showing a configuration of a connecting section of the inner shaft of the rotary self-propelled endoscope of the embodiment.
Figure 8:
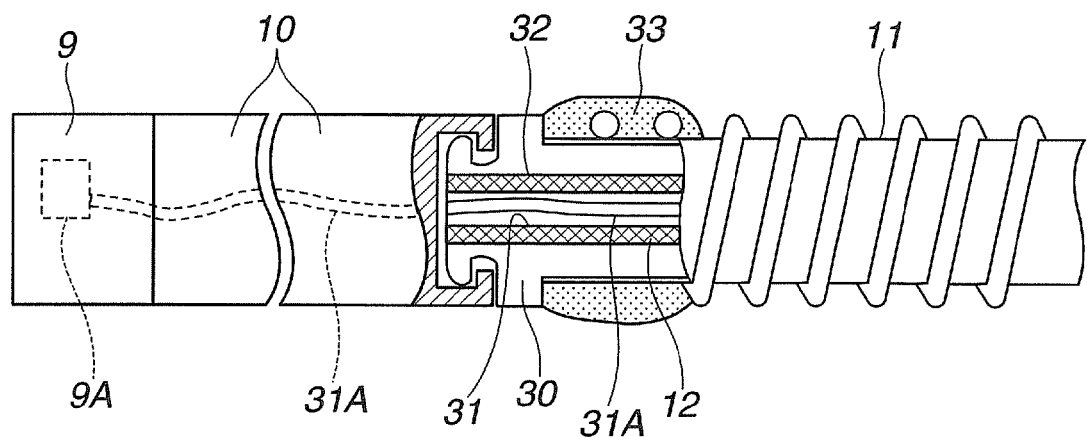
FIG. 8 is a main part enlarged view showing a configuration of a distal end connecting section of the insertion section of the rotary self-propelled endoscope of the embodiment, with a part thereof shown in cross-section.
Figure 9:
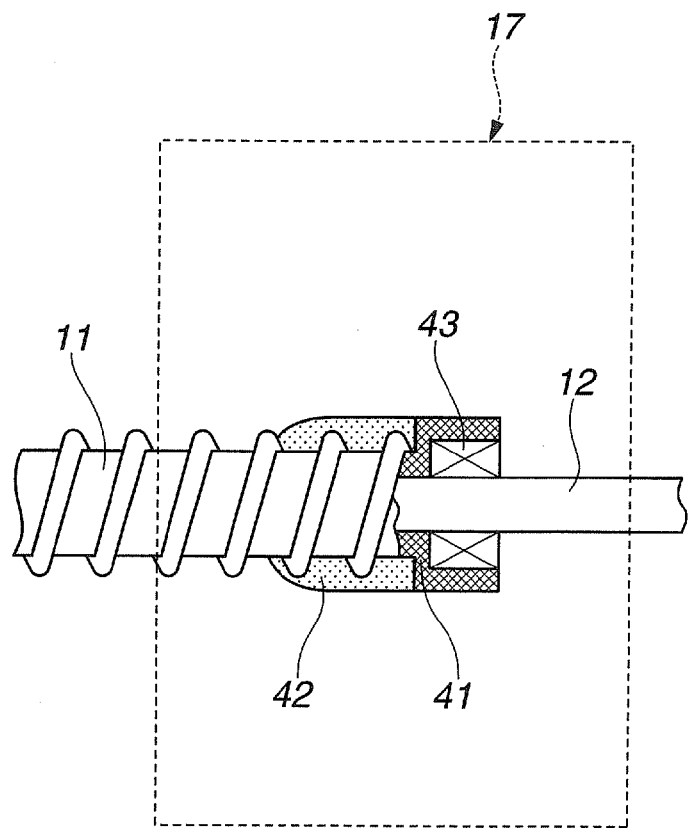
FIG. 9 is a configuration view showing a configuration of a coupling section of the rotary self-propelled endoscope of the embodiment.
Figure 10:
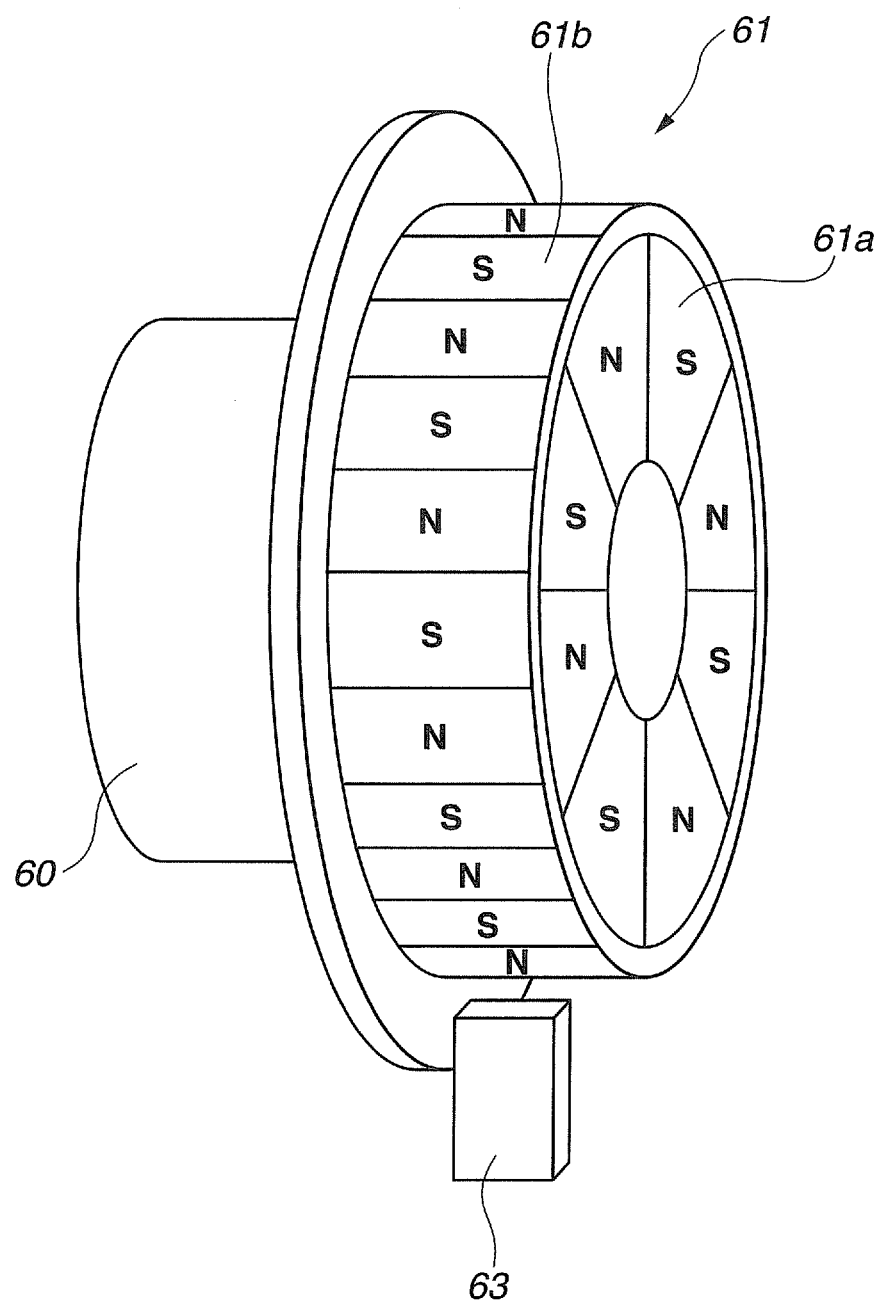
FIG. 10 is a perspective view showing a configuration of a magnet magnetizing pattern and a magnetic sensor in the motor box of the rotary self-propelled endoscope of the embodiment.
Figure 11:
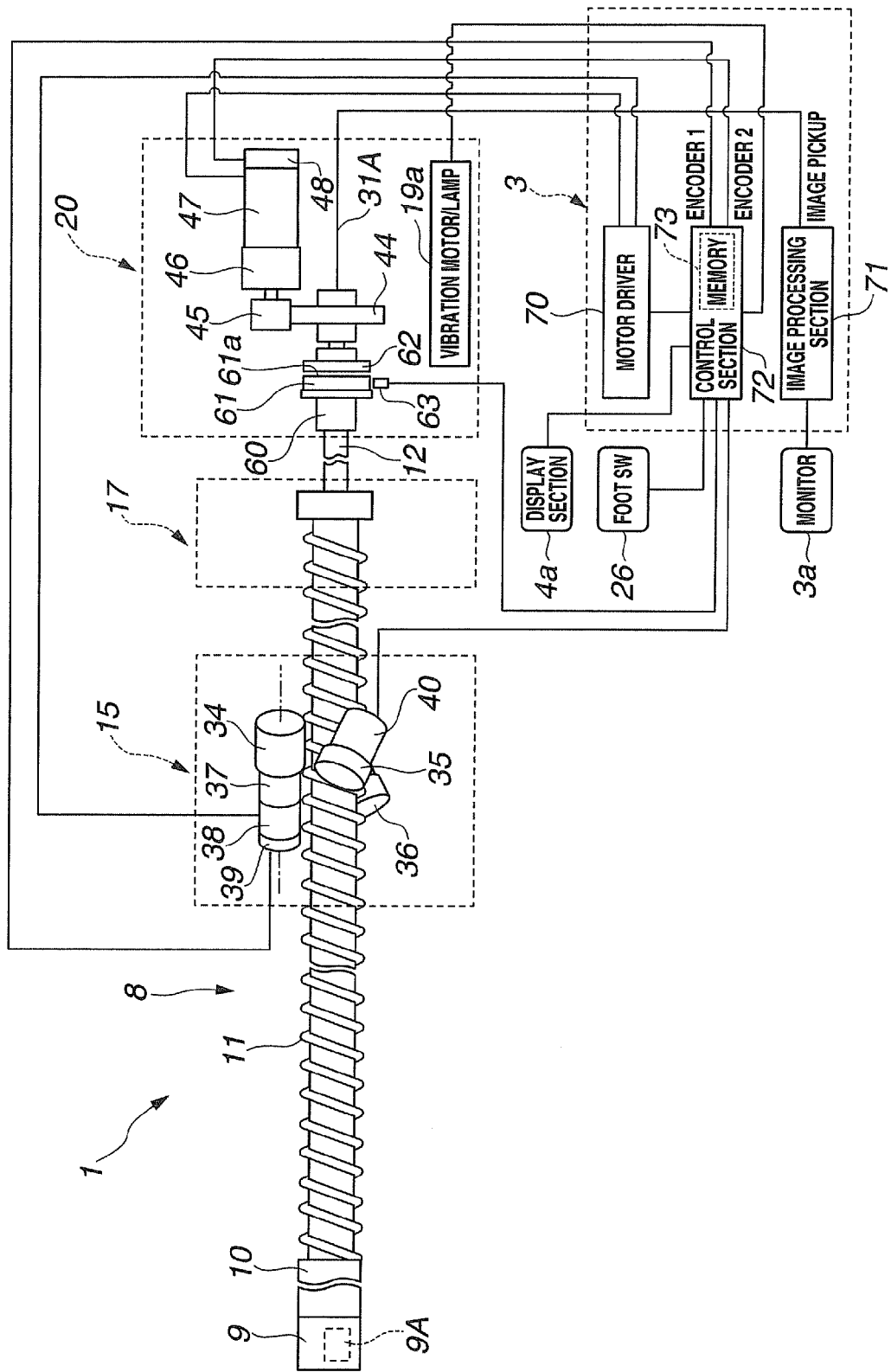
FIG. 11 is a block diagram showing a configuration of an electric circuit of the entire endoscope system having the rotary self-propelled endoscope of the embodiment.
Figure 12:
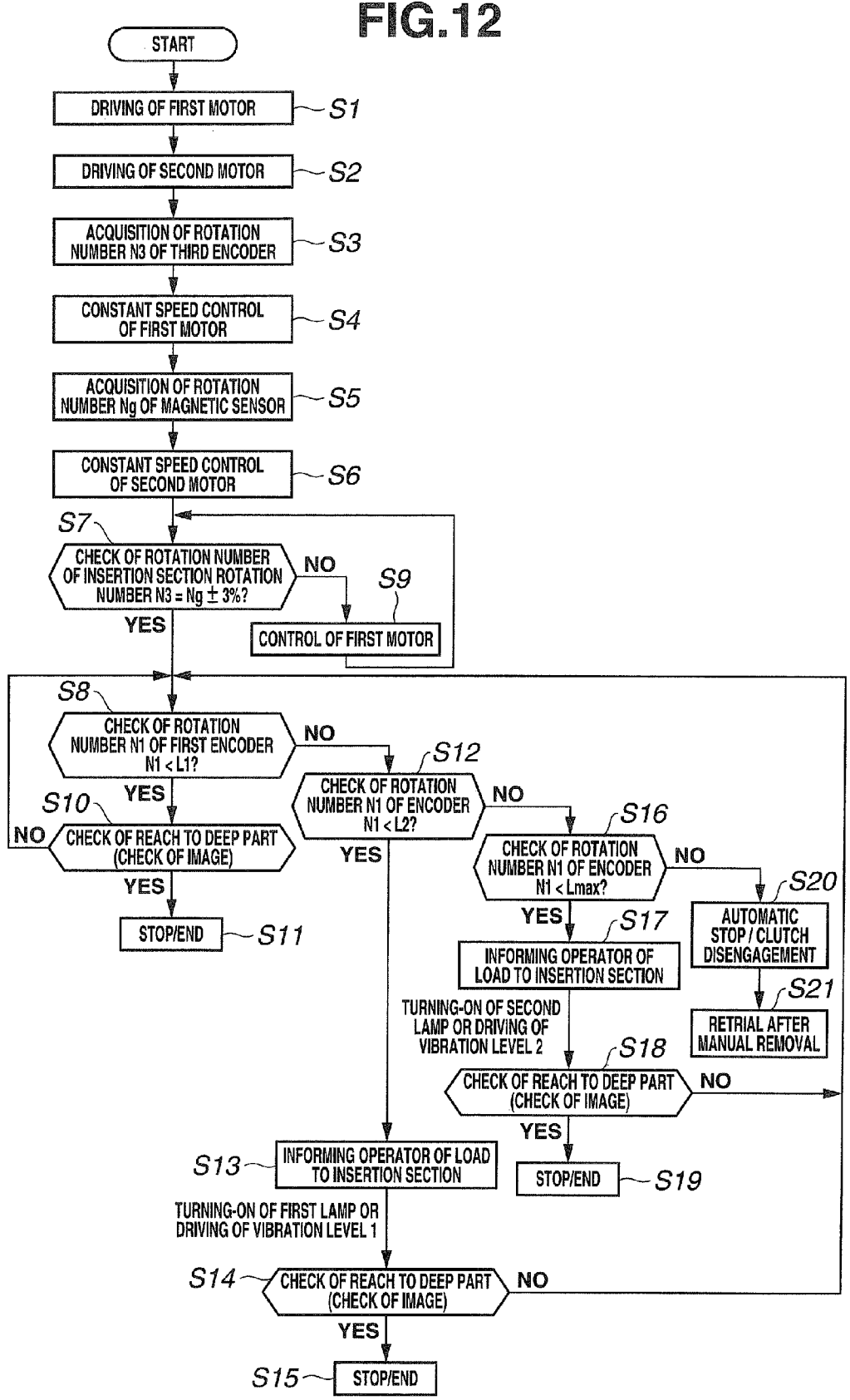
FIG. 12 is a flowchart showing a control by a control section of the rotary self-propelled endoscope of the embodiment.
Figure 13:
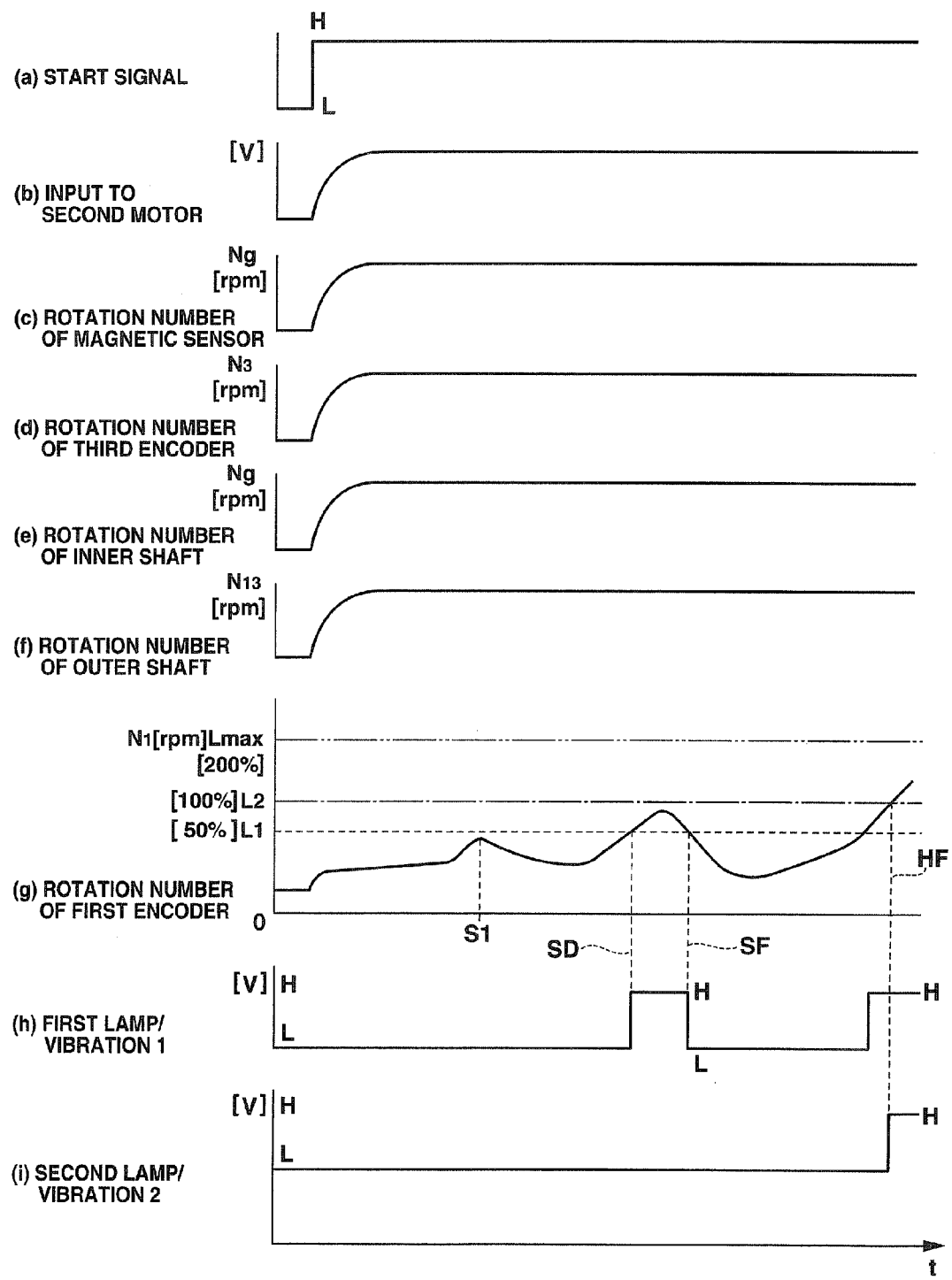
FIG. 13 is a timing chart illustrating a control operation of the control section of the rotary self-propelled endoscope of the embodiment.
Figure 14:
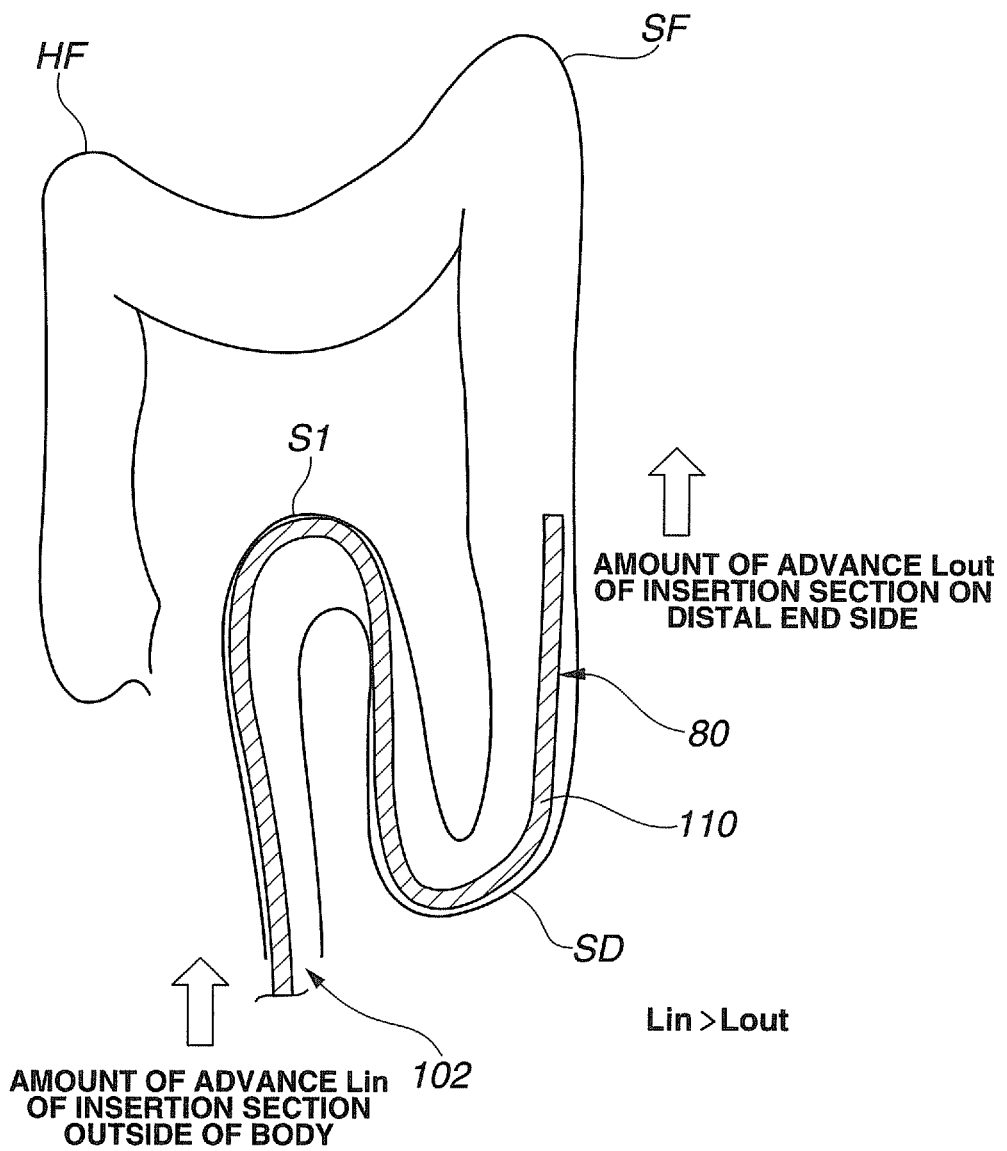
FIG. 14 is an exemplary view illustrating an operation of a rotary self-propelled endoscope of the prior art.
Figure 15:
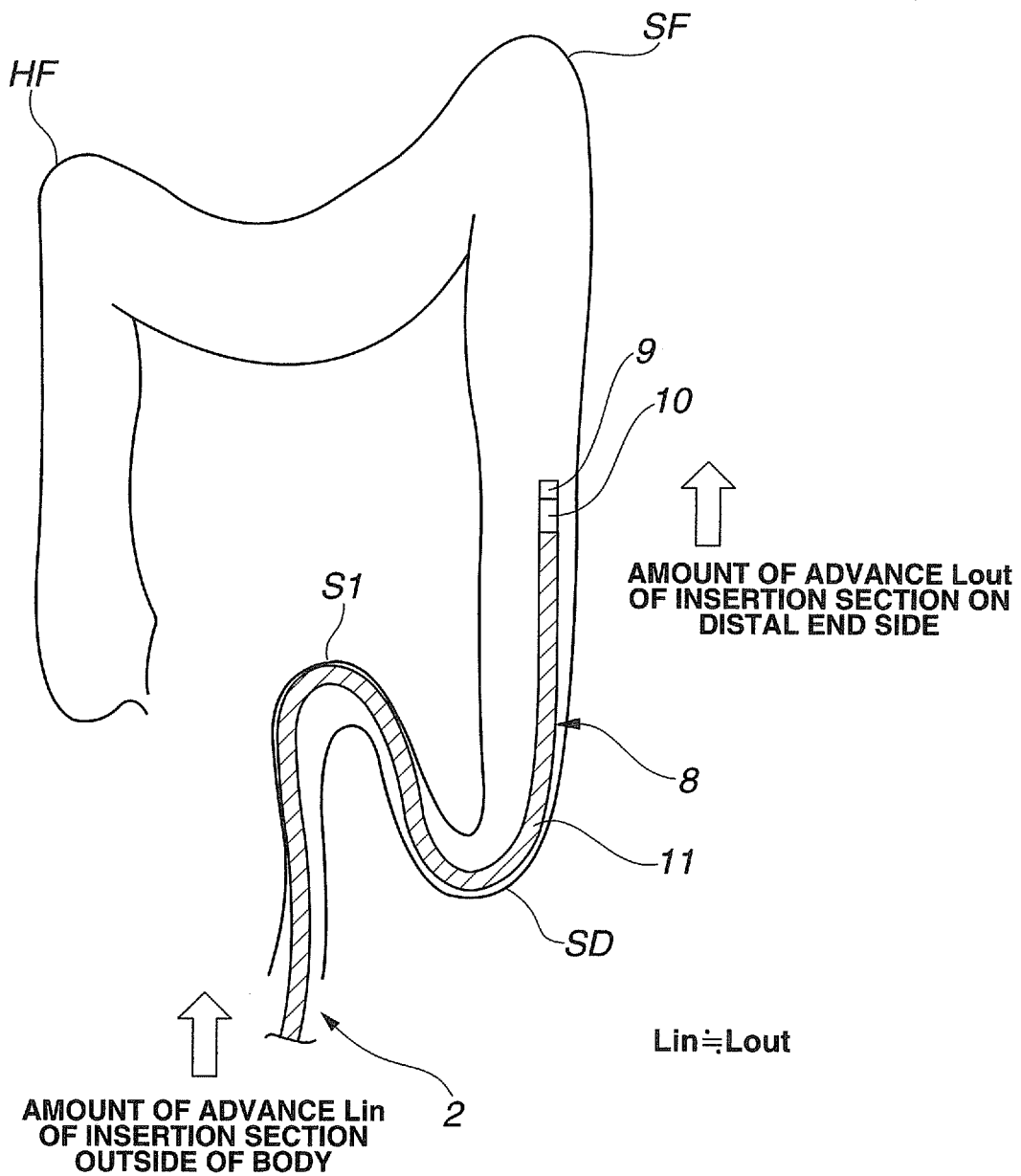
FIG. 15 is an exemplary view illustrating an operation of the rotary self-propelled endoscope of the embodiment.

FIGS. 1 to 15 show an embodiment of the present invention; FIG. 1 is an appearance perspective view showing an entire configuration of an endoscope system having a rotary self-propelled endoscope; FIG. 2 is a configuration view illustrating a configuration of main sections and an insertion section of the rotary self-propelled endoscope; FIG. 3 is a main part enlarged view showing an outer shaft having a helical configuration of the insertion section showing a part thereof in cross-section; FIG. 4 is a main part enlarged view showing an inner shaft which is wired in the outer shaft of the insertion section, with the part thereof shown in cross-section; FIG. 5 is a configuration view showing a configuration of an external drive section; FIG. 6 is a configuration view showing a configuration of a motor box in an operation section; FIG. 7 is a configuration view showing a configuration of a connecting section of the inner shaft; FIG. 8 is a main part enlarged view showing a configuration of a distal end connecting section of the insertion section, with a part thereof shown in cross-section; FIG. 9 is a configuration view showing a configuration of a coupling section; FIG. 10 is a perspective view showing a configuration of a magnet magnetizing pattern and a magnetic sensor in the motor box; FIG. 11 is a block diagram showing an electric circuit configuration of the entire endoscope system; FIG. 12 is a flowchart showing a control by control section; FIG. 13 is a timing chart illustrating a control operation of the control section; FIG. 14 is an exemplary view illustrating an operation of a rotary self-propelled endoscope of the prior art; and FIG. 15 is an exemplary view illustrating an operation of a rotary self-propelled endoscope of the present embodiment.

First, in conjunction with FIG. 1, the entire configuration of an endoscope system having a rotary self-propelled endoscope of the present embodiment will be explained below.

As shown in FIG. 1, an endoscope system 1 has a rotary self-propelled endoscope (hereinafter, simply referred to as an "endoscope") 2 of the present embodiment, a first control device 3, a monitor 3a, a second control device 4, and an aspirator 5. The endoscope 2 has an insertion section 6 and an operation section 7.

The insertion section 6 has in an order from the distal end thereof: an insertion section main body 8 to be inserted into a luminal cavity having a distal end portion 9 and a bending portion 10; an insertion assistance device 13; an insertion section receiving case 16; a distal end side guide tube 14 which is a corrugated tube interposed between the insertion assistance device 13 and the insertion section receiving case 16; an external drive section 15 which is a second drive section; a coupling section 17 which is provided on the operation section side of the insertion section receiving case 16; and an operation section side guide tube 18 which is a corrugated tube interposed between the operation section 7 and the coupling section 17.

The operation section 7 has a motor unit 20 which is a first drive section, a grasping section 21, and a main operation section 22 which is an operation instruction section. The motor unit 20 is configured with a motor box 19 which has a lamp 19a on the outer surface thereof, and the motor box 19 is also one element included in the insertion section 6. The motor box 19 has a motor for applying torque to an inner shaft 12 which is a torque transmitting member as described later, and other components incorporated therein.

The operation section 22 is provided with a bending operation knob 23A for bending the bending portion 10 of the insertion section 6 into the four upward, downward, leftward and rightward direction, operation buttons 23 for delivery operations and suction operations of fluids, and operation switches 24 for operating optical systems for image pickup, lighting, and the like.

The bending operation knob 23A includes two operation knobs: a vertical bending operation knob 23x for operating the bending portion 10 in the upward and downward directions; and a lateral bending operation knob 23y for operating the bending portion 10 in the leftward and rightward directions, with each of the bending operation knobs 23x and 23y being formed into a generally disk like shape. The two operation knobs are rotatably disposed on the outer surface of the main operation section 22 of the operation section 7, in a state of being coaxially superposed on each other.

The vertical bending operation knob 23x is mounted closer to the outer surface of the main operation section 22, and the lateral bending operation knob 23y is coaxially mounted in a state of being superposed on the vertical bending operation knob 23x. Thus, the vertical bending operation knob 23x is disposed closer to the main operation section 22 than the lateral bending operation knob 23y, which facilitates the use of the vertical bending operation knob 23x that is more frequently used in a normal operation of the endoscope 2.

The main operation section 22 has a side surface from which a universal cord 22a is extended outward through which an electric cable and the like are inserted. At the root of the main operation section 22 from which the universal cord 22a is extended, a bend preventing portion 22b is provided. The universal cord 22a is connected to a rear portion of the first control device 3 via a connector (not shown).

The first control device 3 controls a processing of a picked up image, an electrical supply to LEDs which are the lighting section, and an electrical supply to each motor provided in the motor box 19, based on the various switch operations of the main operation section 22.

Also, not shown, but the first control device 3 is connected to the rear portion of the second control device 4. That is, every operation instruction given by the operations of a part of the switches and the operations of operation buttons 23 disposed on the main operation section 22 to the second control device 4 having a display section 4a is transmitted through the universal cord 22a to the second control device 4 via the first control device 3.

The first control device 3 is connected with a footswitch 26 via an electric cable 26a, which enables an operation to start or stop the rotations of an outer shaft 11 which is a rotary cylindrical body and an inner shaft 12 which is a torque transmission member, in a predetermined direction, and the outer shaft 11 and the inner shaft 12 will be explained later.

In addition to the footswitch 26, on/off switches (not shown) for the operations of the outer shaft 11 and the inner shaft 12 in a rotation direction are disposed to predetermined positions on the outer surface of the main operation section 22 of the operation section 7, on the front surface of the control device 3, and the like.

The front surface of first control device 3 are provided with various operation members such as a power switch and operation dials for setting a rotation speed of the outer shaft 11 and the inner shaft 12.

The first control device 3 is connected to the monitor 3a. The monitor 3a displays an endoscope image obtained by the endoscope 2.

The operation buttons 23 which is the operation instruction section disposed on the outer surface of the main operation section 22 includes an air-supply/water-supply button 23a for the operations to supply air or liquid to a subject from the distal end portion 9, a suction button for the operation to suck body fluid and the like from the subject through the distal end portion 9, and an operation button 23c for other functions.

The motor box 19 has four tubes 25 extending therefrom to be inserted in the insertion section 6. The four tubes 25 include an air-supply tube 25a, a water-supply tube 25b, a suction tube 25c, and an extra tube 25d. Without the extra tube 25d, only three tubes may be provided. The four tubes 25 have ends which are individually coupled to predetermined positions on the front surface of the second control device 4 via removable connectors.

A predetermined operation of the air-supply/water-supply button 23a of the main operation section 22 causes the control device 3 to control a suction pump and valves (not shown) to operate, and as the result of that distilled water, physiological saline, or the like from a water-supply tank is ejected from an opening (not shown) formed in the distal end portion 9 toward the front surface of the distal end portion 9 through the water-supply tube 25b.

A predetermined operation of the air-supply/water-supply button 23a of the main operation section 22 causes the second control device 4 to control a compressor and valves (not shown) to operate, and as the result of that air from the compressor is ejected from an air-supply opening (not shown) formed in the distal end portion 9 through the air-supply tube 25a.

The second control device 4 is connected with the aspirator 5 via a tube 5a. The tube 5a is linked to the suction tube 25c which is connected to the front surface of the second control device 4 via a connector. In the endoscope system 1, the aspirator 5 is used as an example of a separate element connected to the second control device 4, but instead of the aspirator 5, an aspiration system equipped to hospital or facility may be used, for example.

A predetermined operation of the suction button 23b of the endoscope 2 causes the second control device 4 to control a suction pump and valves (not shown) to operate, and as the result of that body fluid or the like of a subject is sucked through a suction channel opening (not shown) in the distal end portion 9. The sucked body fluid or the like is sent through the suction tube 25c to the aspirator 5 connected to the second control device 4 by the tube 5a.

Next, in conjunction with FIG. 2, the detailed configuration of the distal end portion 9 and the insertion section main body 8 having the bending portion 10 which constitute a part of the insertion section 6 of the endoscope 2, and the configuration of the main parts of the endoscope 2 will be explained below.

As shown in FIG. 2, the insertion section main body 8 which constitutes a part of the insertion section 6 is an elongated and tubular element with a distal end portion, which is rotatable around the longitudinal axis and at least partially has a surface formed to have a helical configuration, and specifically, the insertion section main body 8 has the distal end portion 9, the bending portion 10, the outer shaft 11 which is a tubular rotary cylindrical body rotatable around its longitudinal axis and at least partially has a surface formed to have a helical configuration, and the inner shaft 12 which is a torque transmitting member rotatably inserted through the outer shaft 11 and coupled to the distal end portion 9. A contact of the outer shaft 11 having a helically shaped portion with a wall of a luminal cavity generates propulsion for insertion. Therefore, the propulsion can be obtained more easily when the outer shaft 11 has a longer helically shaped portion. However, the helical configuration does not have to be formed all along the length of the outer shaft 11, but may be formed on at least a part of the surface: a helical configuration on 20% or more of the total length of the outer shaft 11 enables driving for insertion, and in many cases a helical configuration on 50% or more of the total length enables driving for insertion without problems.

The outer shaft 11 is caused to rotate around its longitudinal axis by the external drive section 15 which is a second drive section as explained later. And the inner shaft 12 inserted through the outer shaft 11 is caused to rotate around its longitudinal axis by the motor unit 20 which is a first drive section, the motor unit 20 being installed on the proximal end side of the insertion section main body 8. The external drive section 15 is disposed at a position closer to the distal end side of the insertion section main body 8 than the position of the motor unit 20 for transmitting driving force from the outer peripheral side of the outer shaft 11 to rotate the outer shaft 11.

The insertion section receiving case 16 into which the insertion section main body 8 is received has a coupling section 17 on the operation section side thereof. The coupling section 17 rotatably holds one end of the outer shaft 11, and rotatably holds the inner shaft 12.

As shown in FIG. 2, each end of the outer shaft 11 and the inner shaft 12 on the distal end portion 9 side is fixed to a distal end supporting section 30 which is rotatably linked to the distal end portion 9 and the bending portion 10 via adhesive joints 32 and 33, respectively.

The detailed configuration of the main parts of the endoscope 2 will be explained in conjunction with FIG. 3 to FIG. 10.

The outer shaft 11 has a surface having a helical configuration, and is rotatably disposed on the outer periphery of the inner shaft 12 around the axis of the inner shaft 12, so as to function as a propulsion generating section. As shown in FIG. 3, the outer shaft 11 is formed with a coil 11a which is wound not densely and a resin thin film 11b which links between the striae of the coil 11a.

The coil 11a is made of a biocompatible metal which does not include nickel or resin, for example. The wire of the coil 11a has a generally circular cross section, and has a diameter on the order of 1.0 mm in consideration of catch with a wall of a luminal cavity. The coil 11a has a helix angle (lead angle) within a range of 9 degrees to 15 degrees for example, so as to obtain a propelling speed which is preferable for endoscopy. That is, as shown in FIG. 3, the resin thin film 11b is provided in a form for covering the outer periphery of the coil 11a so that the resin thin film 11b join between the striae of the coil 11a, thereby the striae of the coil 11a are linked by the resin thin film 11b. The resin thin film 11b is made of a resin which has Shore A hardness (ISO 808) of 50 to 90 degrees for example to have a thickness of 0.03 to 0.2 mm in consideration of flexibility and durability. The resin thin film 11b is made of a biocompatible resin having good slidability, flexibility, and formability, such as urethane, thermoplastic resin, and polyester so as to have a clear, translucent, or dark color.

The outer shaft 11 can have the helical configuration with high ridge portions because the resin thin film 11b links between the striae of the coil 11a and covers the outer periphery of the coil 11a. Thus, the outer shaft 11 is easy to be caught by wall of a luminal cavity, which generates high propulsion. Also, the coil 11a is used to form the helical configuration of the outer shaft 11, which allows the helix angle and other conditions to be set as desired, and prevents a complicated configuration. In addition, the outer shaft 11 is formed with a coil 11a which is not densely wound for a light weight, which maintains good operability of the insertion section main body 8 including the distal end portion 9 and the bending portion 10.

Next, as shown in FIG. 4, in order to reduce the generation of torsion of the insertion section main body 8 and rotate the distal end portion 9 of the insertion section main body 8 with a good following capability to the proximal end side, the inner shaft 12 is configured to have anti-torsion property.

That is, in order to obtain anti-torsion property, the inner shaft 12 is formed with a coil 12a which is wound not densely in the same normal direction as that of the coil 11a of the inner shaft 12, a coil 12b which is wound not densely in the direction opposite to that of the coil 12a to be disposed between the striae of the coil 12a, a coil 12c which is wound not densely in the normal direction, that is the opposite direction to that of the coil 12b, to be disposed between the striae and on the outer periphery of the coil 12b, and a resin thin film 12d which links between the striae of the coil 12c.

The coils 12a to 12c are made of a biocompatible metal which does not include nickel or resin, for example. The wire of the coil 12a to 12c has a generally circular cross section for example, but the coil 12a to 12c may be made of a rectangular coil which has a rectangular cross section. As shown in FIG. 4, the resin thin film 12d is provided in a form for covering the outer periphery of the coil 12c so that the resin thin film 12d joins between the striae of the coil 12c, thereby the striae of the coil 12c are link by the resin thin film 12d.

The resin thin film 12d is made of a biocompatible resin having good slidability, flexibility, and formability, such as urethane, thermoplastic resin, and polyester so as to have a clear, translucent, or dark color.

In this way, the inner shaft 12 is configured with a three-layered winding structure of the coils 12a to 12c, which allows the inner shaft 12 to have anti-torsion property, and allows the distal end portion 9 which is coupled thereto to rotate with good following capability to the rotation of the motor unit 20, that is the proximal end side. In addition, the inner shaft 12 is formed with the coil 12a to 12c which are not densely wound for a light weight, which maintains good operability of the insertion section main body 8.

The inner shaft 12 may be configured with a four or more layered winding structure, or with a three-layered winding structure using coils closely wound with four or eight striae.

Next, with FIG. 2 and FIG. 5, the configuration of the external drive section 15 which constitutes the second drive section will be explained below. As shown in FIG. 2, the external drive section 15 has: at least three rotating rollers (a first roller 34, a second roller 35, a third roller 36); a gear box 37 connected to the first roller 34; a first motor 38 for rotating the first roller 34 which is a rotation drive source; a first encoder 39 for detecting a rotation amount of the first roller 34; and a third encoder 40 for detecting a rotation amount of the second roller 35.

That is, the first roller 34 is the driving roller which transmits rotational drive force to the outer shaft 11; the second roller 35 is a roller for detecting a rotation number; and the third roller 36 is a fixed roller to press each roller against the outer shaft 11. Any large load applied to the rotation of the outer shaft 11 from outside causes so-called slip phenomena at the contact between the first roller 34 and the outer shaft 11, and as the result of that the rotation of the first roller 34 is not completely transmitted to the outer shaft 11.

The first motor 38 transmits torque to the first roller 34 via the gear box 37. The rotation number of the first motor 38 is detected by the first encoder 39, and the signal of the rotation number is outputted to the motor driver 70 (see FIG. 11) of the first control device 3 which will be explained later.

The two of the second roller 35 and the third roller 36 are disposed at positions on the outer shaft 11 of the insertion section main body 8 which are different from that of the first roller 34. The second and third rollers 35 and 36 have water-absorbing sheets (not shown) wound around at the positions on both end sides which can be in contact with the outer shaft 11. The water-absorbing sheet absorbs soils which are attached to the outer surface of the insertion section main body 8 when the insertion section main body 8 is received after the insertion to and removal from a luminal cavity.

The first roller 34, the second roller 35, and the third roller 36 are disposed with each of the rotation shaft being inclined relative to the direction of the longitudinal axis of the insertion section main body 8. That is, the first roller 34, the second roller 35, and the third roller 36 are disposed to be inclined so that the circumferential direction of each periphery surface is generally along the direction of the helical configuration formed on the surface of the outer shaft 11. This arrangement is done with the purpose to transmit torque smoothly to the outer shaft 11 without disturbing the advancing and retracting of the insertion section main body 8 which is caused by the rotation of the outer shaft 11. However, as shown in FIG. 5, the external drive section 15 may be configured with the first motor 38 which is removable from the first roller 34 for example.

The external drive section 15 has a first housing 15A and a second housing 15B. The second housing 15B is provided with the first motor 38, the gear box 37, and the first encoder 39. The gear box 37 has a driving shaft extending therefrom to the outside of the second housing 15B, and the driving shaft is provided with a gear 57.

To the contrary, the first housing 15A is provided with the first roller 34, the second roller 35, and the third roller 36. The first roller 34 has a rotation shaft extending therefrom to the outside of the first housing 15A, and the rotation shaft is provided with a gear 58. The gear 58 has a rotation shaft which is provided with an O ring 59 on the outer periphery in the first housing 15A, so that the inside of the first housing 15A and the gear 58 are configured in a water-tight manner. When the first housing 15A is mounted to the second housing 15B, the gear 57 on the second housing 15B side meshes with the gear 58 on the first housing 15A side. The above described configuration enables removal the second housing 15B with the first motor 38 for reuse. Moreover, even if soils are attached to the outer shaft 11 or other elements of the insertion section main body 8, since the inside of the first housing 15A is kept water-tight relative to the second housing 15B due to the O ring 59, the second housing 15B can be kept in a clean state.

Next, in conjunction with FIG. 2, FIG. 6, and FIG. 7, the configuration of the motor unit 20 which constitutes the first drive section will be explained below. As shown in FIG. 2 and FIG. 6, the motor unit 20 in the operation section 7 includes a second motor 47 which is a rotation drive source for rotating the inner shaft 12, and a magnetic clutch having a first yoke 60, a second yoke 62, and a magnet section 61 for cutting off the transmission of torque from the second motor 47 when a predetermined load is applied thereto.

The motor unit 20 has the first yoke 60 and magnet section 61 to which one end of the inner shaft 12 is fixed, the second yoke 62, a magnetic sensor 63 for detecting a rotation number of the first yoke 60, a third gear 44 by which the rotation shaft of the second yoke 62 is supported, a second gear 45 which meshes with the third gear 44, a gear box 46 coupled to the rotation shaft of the second gear 45, the second motor 47 which is the drive source for rotating the rotation shaft of the gear box 46, and a second encoder 48 for detecting a rotation number of the second motor 47.

As shown in FIG. 7, the end of the inner shaft 12 is fixed to the first yoke 60 by the adhesive joint 64 with the inner shaft 12 being through the cylindrical first yoke 60 which is fixed to the disk-shaped magnet section 61. The inner shaft 12 and the first yoke 60 may be fixed to each other by a screw for example.

The second motor 47 transmits torque to the second gear 45 via the gear box 46. A rotation number of the second motor 47 is detected by the second encoder 48, and the signal of the rotation number detected by the second encoder 48 is outputted to the motor driver 70 of the first control device 3 (see FIG. 11).

The second gear 45 meshed with the third gear 44 transmits torque to the second yoke 62 via the shaft member. The second yoke 62 is disposed at a position opposite to the first yoke 60 and magnet section 61 to which the end of the inner shaft 12 is fixed, via a gap 61c which corresponds to the torque amount to be transmitted.

The first yoke 60 and the second yoke 62 are formed with a soft magnetic material with which a magnetic circuit is configured in order to efficiently use the magnetic force. On the second yoke 62 side also, another magnet section may be provided to oppose to the magnet section 61. The first yoke 60 and the magnet section 61 and the second yoke 62 are indirectly coupled with each other by the magnetic force in spite of the gap 61c, thereby the torque of the second yoke 62 is transmitted to the magnet section 61 and the first yoke 60.

That is, the torque of the second motor 47 is transmitted to the magnet section 61 and the first yoke 60 via the gear box 46, the gear 45, the gear 44, the second yoke 62, and causes the inner shaft 12 to rotate around its longitudinal axis. Then a rotation number of the first yoke 60 and the magnet section 61, that is, a rotation number of the inner shaft 12 is detected by the magnetic sensor 63. As shown in FIG. 10, the magnetic sensor 63 is provided near the outer periphery of the magnet section 61, and detects a rotation of the magnet section 61 using a magnetizing pattern 61b formed on the outer periphery of the magnet section 61. The magnetizing pattern 61b is formed by plastic magnets for example, and is multipole magnetized around the outer periphery. The detected result by the magnetic sensor 63 is outputted to the control section of the first control device 3 (see FIG. 11).

The magnet section 61 is provided with a magnetizing pattern section for coupling 61a for coupling the second yoke 62 by magnetic force, at the end surface of the magnet section 61 on the second yoke 62 side. The magnetizing pattern section for coupling 61a is a multipole magnetized plane for improved efficiency of the magnetic force which uses sintered metallic magnets for example.

The above described configuration ensures the detection of a rotation number of the inner shaft 12 of the insertion section main body 8, and also enables the detection of a rotation number of the second motor 47, which allows a control section 72 to compare the rotation number of the inner shaft 12 with that of the second motor 47, thereby a state that the first yoke 60 and the second yoke 62 are separated from each other due to a large load for example can be detected.

As shown in FIG. 2, the inner shaft 12 is inserted through the outer shaft 11 via the coupling section 17.

And as shown in FIG. 9, the inner shaft 12 is rotatably supported by a bearing 43 in a holder 41 of the coupling section 17. The holder 41 on the distal end portion 9 side is fixed to the proximal end of the outer shaft 11 by an adhesive joint 42. That is, the holder 41 rotatably supports the outer shaft 11 relative to the inner shaft 12. In order to increase the adhesive strength between the outer shaft 11 and the holder 41, the outer shaft 11 and the holder 41 may be fixed using an adhesive or the like after being fastened together by a thread.

Next, in conjunction with FIG. 8, the coupling structure of the outer shaft 11 and inner shaft 12 with the distal end portion 9 will be explained below. As shown in FIG. 8, each distal end of the outer shaft 11 and the inner shaft 12 is fixed to the distal end supporting section 30 which is rotatably connected relative to the distal end portion 9 and bending portion 10, via the adhesive joints 32 and 33. The distal end supporting section 30 has an insertion hole formed therein to insert the inner shaft 12 therethrough, the outer peripheral surface of the inner shaft 12 is fixed to the inner peripheral surface of the insertion hole by the adhesive joint 32. While, the outer peripheral surface of the distal end supporting section 30 is fixed to the outer shaft 11 by the adhesive joint 33 with the outer shaft 11 fitting around the distal end supporting section 30. That is, the distal end supporting section 30 also functions as a connector between the outer shaft 11 and the inner shaft 12. In order to increase the adhesive strength of the outer shaft 11, the outer shaft 11 may be fixed using an adhesive or the like after being fastened by a thread.

And as shown in FIG. 8, a cable tube 31 has a cable 31a therethrough which is connected to an image pickup device 9A in the distal end portion 9 and sends/receives signals, and is inserted through the inner shaft 12 via the bending portion 10 and the distal end supporting section 30.

The cable tube 31 inserted through the inner shaft 12 has a proximal end which extends out via the magnet section 61, the second yoke 62, and the gear 44 in the motor unit 20, to be connected to the image process section 71 in the first control device 3 (see FIG. 11).

Next, in conjunction with FIG. 11, a configuration of the rotation drive control of the outer shaft 11 and inner shaft 12 in the endoscope system 1 will be explained below. As shown in FIG. 11, the first control device 3 has the motor driver 70, an image process section 71, and the control section 72.

The motor driver 70 is connected to the first motor 38 of the external drive section 15 and the second motor 47 of the motor unit 20. The first encoder 39 for detecting a rotation number of the first motor 38 of the external drive section 15, the third encoder 40 for detecting a rotation number of the second roller 35 of the external drive section 15, and the second encoder 48 for detecting a rotation number of the second motor 47 of the motor unit 20 are connected to the control section 72.

The control section 72 obtains the values of the rotation numbers of and of the loads on the motor 38, the motor 47, the outer shaft 11, and the inner shaft 12 based on the outputs from each of the first encoder 39, the second encoder 48, and the third encoder 40, the voltage which indicates the load on the first motor 38, and the voltage which indicates the load on the second motor 47, and causes the motor driver 70 to control the rotation numbers of the motors 38 and 47. That is, the first control device 3 controls the external drive section 15 which is the second drive section and the motor unit 20 which is the first drive section to synchronize with each other.

In the present embodiment, the control section 72 controls the rotation number of the first motor 38 based on the rotation number of the inner shaft 12 caused by the second motor 47 as a reference so that the rotation number of the outer shaft 11 becomes generally the same as that of the inner shaft 12.

The control section 72 is also provided with a memory 73 in which a plurality of thresholds are recorded for switching of controls when a large load is applied to the outer shaft 11 after the insertion section main body 8 is advanced to a deeper part of a body cavity. The control section 72 compares the plurality of thresholds with a detected result by the first encoder 39, and when the result exceeds the individual thresholds, in order to inform the operator of the comparison result, the control section 72 controls a vibration motor (not shown) and a lamp 19a provided in the operation section 7. The vibration motor has a vibration section, and the lamp 19a has a lamp such as an LED, thereby a warning can be given to the operator by driving at least one of the vibration section and the lamp.

The threshold indicates a rotation number of the first motor 28 when a load is applied to the outer shaft 11. That is, as already described, a load applied to the outer shaft 11 causes slip phenomena at the contact between the first roller 34 and the outer shaft 11, and as the result of that the rotation of the first motor 28 is not efficiently transmitted to the outer shaft 11. To avoid the situation, the control section 72 controls to increase the rotation number of the first motor 28 so that the outer shaft is rotated at a predetermined constant speed. Therefore, using a change of the rotation number of the first motor 28 relative to the rotation number of the outer shaft 11, the amount of load applied to the outer shaft 11 can be assumed.

For example, the rotation number which is increased by 50% of the rotation number of the outer shaft 11 is set to be a threshold L1, the rotation number which is increased by 100% of the rotation number of the outer shaft 11 is set to be a threshold L2, and the rotation number which is increased by 200% of the rotation number of the outer shaft 11 is set to be a threshold Lmax. Of course, these thresholds are variously settable.

Next, in conjunction with FIG. 12 and FIG. 13, the operation flow of driving for rotation of the insertion section main body 8 while the external drive section 15 (second drive section) and the motor unit 20 (first drive section) are controlled to synchronize with each other in the endoscope system 1 will be explained in the context of an insertion into large intestine.

In FIG. 13, the (a) shows a start signal in a rotation drive control; the (b) shows a driving voltage inputted to the second motor 47; the (c) shows a rotation number detected by the magnetic sensor 63; the (d) shows a rotation number detected by the third encoder 40; the (e) shows a rotation number of the inner shaft 12; the (f) shows a rotation number of the outer shaft 11; the (g) shows a rotation number and a plurality of thresholds detected by the first encoder 39; the (h) shows an on/off signal of the first lamp/vibration 1; and the (i) shows an on/off signal of the first lamp/vibration 2. The rotation number (c) is equal to that of (e), and the rotation number (d) is equal to that of (f). The horizontal axis represents time, that is, the position of the distal end portion in large intestine.

Now, the operations will be explained below in accordance with the flowchart of FIG. 12.

Receiving an instruction from an operator to rotate the outer shaft 11 and the inner shaft 12 through the footswitch 26 or the like, the control section 72 starts to drive the first motor 38 in the external drive section 15 at Step S1, and starts to drive the second motor 47 in the motor unit 20 at Step S2.

At Step S3, the control section 72 obtains a rotation number N3 (see FIG. 13(d)) from the third encoder 40, and controls the external drive section 15 to rotate the first motor 38 at a constant speed (a normal constant speed for a predetermined rotation number of the first motor 38) in response to the rotation number N3 at Step S4.

Next, the control section 72 obtains a rotation number Ng (see FIG. 13(c)) from the magnetic sensor 63 at Step S5, and at subsequent Step S6, the control section 72 controls the motor unit 20 to rotate the second motor 47 at a constant speed (a normal constant speed for a predetermined rotation number of the second motor 47).

Then, at Step S7, the control section 72 compares the rotation number of the insertion section main body 8, that is the rotation number of the outer shaft 11 (FIG. 13(f)) with the rotation number of the inner shaft 12 (FIG. 13(e)). That is, the control section 72 determines if the rotation number N3 from the third encoder 40 is equal to a value within the range of the rotation number Ng ±3% from the magnetic sensor 63, and if yes, the process goes to Step S8, and if no, the process goes to Step S9 where the control section 72 controls external drive section 15 to change the rotation number of the first motor 38 to be equal to a value within the range, and repeats the operations from Step S7.

At Step S8, the control section 72 obtains a rotation number N1 from the first encoder 39, and determines if the rotation number N1 (see FIG. 13) is smaller than the threshold L1 (see FIG. 13) or not.

When the control section 72 determines that the rotation number N1 from the first encoder 39 is smaller than the threshold L1, the control section 72 checks if the distal end portion 9 of the insertion section main body 8 reaches a target deep part in a body cavity or not at Step S10.

Receiving a check instruction that the distal end portion 9 has reached the deep part from the operator, the control section 72 controls the external drive section 15 and the motor unit 20 to stop the rotations of the outer shaft 11 and the inner shaft 12, and ends the process at Step S11. On the other hand, without the check instruction from the operator, the control section 72 repeats the operations at Step S8 and so on. That is, the endoscope 2 continues the insertion operation.

At Step S8, when the control section 72 determines that the rotation number N1 from the first encoder 39 is larger than the threshold L1 (see FIG. 13), the process goes to the determination process at Step S12.

In the determination process at Step S12, the control section 72 determines if the rotation number N1 from the first encoder 39 is smaller than the threshold L2 (see FIG. 13) which is larger than the threshold L1 or not.

When the control section 72 determines that the rotation number N1 from the first encoder 39 is smaller than the threshold L2, at Step S13, the control section 72 controls the vibration motor and the lamp 19a to inform the operator of the fact that a load was applied to the outer shaft 11.

The load applied to the outer shaft 11 is considered to be caused due to the insertion of the insertion section main body 8 into the part from the flexure SD junction of large intestine shown in FIG. 15, that is the part between sigmoid colon S and colon descendents D, to the splenic flexure (SF), that is between colon transversum and colon descendents, for example. Then, in order to inform the operator of the rotation number level of the outer shaft 11 which is larger than the threshold L1 and less than the threshold L2, that is, the fact that a load was applied to the outer shaft 11, the control section 72 generates a warning signal. For example, the control section 72 controls the vibration motor and the lamp 19a to operate at "Vibration Level 1" (see FIG. 13(h)). The "Vibration Level 1" means a control state in which the vibration section generates weak vibration and the lamp 19a is turned on.

At Step S14, the control section 72 checks if the distal end portion 9 of the insertion section main body 8 reaches a target deep part in a body cavity or not.

At the point, receiving a check instruction from the operator that the distal end portion 9 has reached the deep part from the operator, at subsequent Step S15, the control section 72 controls the external drive section 15 and the motor unit 20 to stop the rotations of the outer shaft 11 and the inner shaft 12, and ends the process. On the other hand, without the check instruction from the operator, the control section 72 repeats the operations at Step S8 and so on. That is, the endoscope 2 continues the insertion operation.

When the control section 72 determines that the rotation number N1 from the first encoder 39 is larger than the threshold L2 (see FIG. 13) based on the process at Step S12, the process goes to the determination process at Step S16.

In the determination process at Step S16, the control section 72 determines if the rotation number N1 from the first encoder 39 is smaller than the threshold Lmax (see FIG. 13) or not. When the control section 72 determines that the rotation number N1 from the first encoder 39 is smaller than the threshold Lmax, at Step S17, the control section 72 controls the vibration motor and the lamp 19a to inform the operator of the fact that a large load was applied to the outer shaft 11 but the insertion operation can be continued.

In the case, the load applied to insertion section main body 8 is considered to be caused due to the insertion of the insertion section main body 8 into the part from splenic flexure (SF) to hepatic flexure (HF) shown in FIG. 15, for example. Then, in order to inform the operator of the dangerous rotation number level of the outer shaft 11 which is close to the threshold Lmax, that is, the fact that a large load was applied to the outer shaft 11, the control section 72 controls the vibration motor and the lamp 19a to operate at "Vibration Level 2" (see FIG. 13(i)). The "Vibration Level 2" means the control state in which the vibration section generates strong vibration and the lamp 19a is flashing, for example.

Then, the control section 72 checks if the distal end portion 9 of the insertion section main body 8 has reached the target deep part in the body cavity or not at Step S18.

Receiving a check instruction that the distal end portion 9 has reached the deep part from the operator, the control section 72 controls the external drive section 15 and the motor unit 20 to stop the rotations of the outer shaft 11 and the inner shaft 12, and ends the process at subsequent Step S19. While, without the check instruction from the operator, the control section 72 repeats the operation at Step S8. That is, the endoscope 2 continues the insertion operation.

When the control section 72 determines that the rotation number N1 from the first encoder 39 is larger than the threshold Lmax based on the process at Step S12, the process goes to the determination process at Step S20.

At Step S20, since the outer shaft 11 is rotating at a large rotation number which exceeds the threshold Lmax, the control section 72 automatically controls the external drive section 15 and the motor unit 20 to stop the rotations of the outer shaft 11 and the inner shaft 12, and also mechanically separates the first yoke 60 and magnet section 61 from the second yoke 62 and turns off the magnetic clutch.

After that, at Step S21, the control section 72 displays a message such as "Remove manually the insertion section main body 8 from the body cavity" on the monitor 3a so as to prompt the operator for a manual removal of the insertion section main body 8. Moreover, the control section 72 tells the operator to repeat the insertion operation, and upon the start of the insertion operation, the control section 72 repeats the operations at Step S1 and so on.

As shown in FIG. 14, in a rotary self-propelled endoscope 102 of the prior art, when the rotary cylindrical body 110 is driven for rotation from the proximal end side of the insertion section main body 80, at first the insertion section main body 80 is inserted at a set speed, but as the insertion section main body 80 is advanced into flexure SD junction, splenic flexure (SF), and hepatic flexure (HF), torsions of the insertion section main body 80 are generated due to loads which is caused by the reaction of intestine, which often delays the advance of the insertion section main body 80. In the case, the following capability of the distal end portion to the proximal end side is decreased, that is, the amount of advance Lout of the insertion section main body 80 on the distal end side is smaller than the amount of advance Lin of the insertion section main body 80 on the proximal end side. However, the drive section continues to drive the rotary cylindrical body 110 at the set speed regardless of the amount of advance Lout of the distal end portion. As a result, as shown in FIG. 14, the insertion section main body 80 deforms and excessively expands the large intestine. In addition, the deformation of large intestine increases the load due to the reaction of large intestine, which causes the problem that the following capability of the distal end portion to the proximal end side is further decreased.

As described above, since a rotary self-propelled endoscope of the prior art is configured so that a rotational device disposed on the proximal end side of an insertion section main body rotates the proximal end side of a long insertion section, as the insertion section main body is inserted into a deeper part of a body cavity, torsions of the insertion section main body are generated due to the load in the body cavity, which often prevents the torque from the rotational device from being sufficiently transmitted to the distal end of the insertion section main body, and decreases the following capability of the distal end portion to the proximal end side.

To the contrary, the endoscope 2 of the present embodiment has the inner shaft 12 which is rotatably inserted through the outer shaft 11 and coupled to the distal end portion 9, and the motor unit 20 which causes the inner shaft 12 to rotate around its longitudinal axis from the proximal end side of the inner shaft 12. And in the endoscope 2, not only the inner shaft 12 is caused to rotate from the distal end side of the insertion section main body 8 by the motor unit 20, but also the outer shaft 11 is caused to rotate from the proximal end side of the insertion section main body 8 by the external drive section 15 located at a position on the distal end side of the motor unit 20. Furthermore, in the endoscope 2 of the present embodiment, the outer shaft 11 and the inner shaft 12 of the insertion section main body 8 are synchronized with each other to rotate at generally the same rotation number.

Therefore, as shown in FIG. 15, in the endoscope 2, there is little difference between the amount of advance of the distal end portion 9 and that of the insertion section main body 8 on the proximal end side. That is, the amount of advance Lout of the insertion section main body 8 on the distal end side after insertion is generally equal to the amount of advance Lin of insertion section main body 8 outside of the body.

Therefore, as shown in FIG. 15, the endoscope 2 of the present embodiment allows the insertion section main body 8 to be inserted to the deep part HF of large intestine without excessively expanding flexures S1 and SD of sigmoid colon and other of large intestine, unlike an endoscope of the prior art. Moreover, in the endoscope 2 of the present embodiment, torsions of the insertion section main body 8 are not generated much, which can maintain the flexibility of the insertion section main body 8.

As described above, according to the rotary self-propelled endoscope 2 of the present embodiment, the distal end portion 9 of the insertion section main body 8 can be rotated with good following capability to the proximal end side by reducing the torsions of the insertion section main body 8, which improves the insertability of the insertion section 6.

Moreover, in the rotary self-propelled endoscope 2 of the present embodiment, the driving of the inner shaft 12 by the motor unit 20 for rotation contributes to the driving of the outer shaft 11. That is, the outer shaft 11 which generates propulsion for propelling in a luminal cavity is driven by the external drive section 15 from the proximal end side, and also driven by the inner shaft 12 from the distal end side.

That is, the motor unit 20 which is the first drive section is disposed on the proximal end side of the insertion section 6, and inner shaft 12 which is the torque transmitting member is rotated from the proximal end side, so that the outer shaft 11 which is the rotary cylindrical body is rotated via the distal end portion 9, and also the external drive section 15 which is the second drive section is disposed on the outer periphery side of the outer shaft 11 on the distal end portion 9 side of the motor unit 20 which is the first drive section, so that the outer shaft 11 is rotated from the proximal end side.

As described above, the control section 72 controls the motor unit 20 and the external drive section 15 so that the rotation number of the inner shaft 12 caused by the motor unit 20 which is the first drive section and the rotation number of the outer shaft 11 near the external drive section 15 caused by the external drive section 15 which is the second drive section are synchronized with each other. The synchronization means the generally same rotation number; for example, external drive section 15 is controlled to generate a rotation number within the range of the rotation number ±3% of the rotation number of the motor unit 20.

Furthermore, the rotary self-propelled endoscope 2 of the present embodiment includes: the insertion section 6 having the distal end portion 9 and the tubular outer shaft 11 which has a surface of a helical configuration and is rotatable around its longitudinal axis; the inner shaft 12 which is rotatably inserted through the insertion section 6 and is coupled to the distal end portion 9; the first drive section which has the second motor 47 and is disposed on the proximal end side of the insertion section 6 for rotating the outer shaft 11 via the distal end portion 9 by rotating the inner shaft 12 from the proximal end side; the second encoder 48 or the magnetic sensor 63 for detecting a rotation number of the inner shaft 12; the second drive section having the first motor 38 and the first roller 34 which is disposed on the outer periphery of the outer shaft 11 on the distal end portion 9 side of the first drive section and is pressed against the outer shaft 11 for rotating the outer shaft 11 from the proximal end side; the first encoder 39 for detecting a rotation number of the first motor 38; the third encoder 40 for detecting a rotation number of the outer shaft 11 near the first roller 34; and the control section 72 for controlling the first drive section and the second drive section so that the rotation number of the outer shaft 11 near the first roller 34 caused by the first drive section and the rotation number of the inner shaft 12 caused by the second drive section are synchronized with each other.

Also, in the above described rotary self-propelled endoscope 2 of the present embodiment, the control section 72 determines the magnitude of a load on the rotation of the outer shaft 11 based on the rotation number of the first motor 38 detected by the first encoder 39 and the rotation number of the outer shaft 11 detected by the third encoder 40.

Moreover, in the above described rotary self-propelled endoscope 2 of the present embodiment, the control section 72 generates a warning signal in response to the magnitude of a load on the rotation of the outer shaft 11.

This configuration improves the insertability of the insertion section main body 8 of the rotary self-propelled endoscope 2 into a luminal cavity.

Specifically, the rotary self-propelled endoscope 2 of the present embodiment has the insertion section main body 8 which can be inserted into a deep part of large intestine without excessively expanding flexures of large intestine.

In the above description, the rotary self-propelled endoscope 2 has the bending portion 10 at the insertion section main body 8, but the present invention is applicable a rotary self-propelled endoscope which does not have the bending portion 10 at the insertion section main body 8, which provides the same effects.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A rotary self-propelled apparatus for introducing visualization apparatus within a luminal cavity, the visualization apparatus having an imager configured to visualize an interior surface of the luminal cavity, the rotary self-propelled apparatus comprising:

an outer shaft having a distal end and a proximal end, a longitudinal axis extending between the distal end and the proximal end, a lumen being configured to receive the visualization apparatus along the longitudinal axis such that when the outer shaft receives the visualization apparatus, the imager of the visualization apparatus will be disposed in a distal position to the distal end of the outer shaft, the outer shaft being configured to form a helical configuration along the longitudinal axis at least partly on an outer surface of the outer shaft;

a torque transmitting member disposed within the outer shaft, the torque transmitting member comprising an inner shaft extending from a proximal side of the outer shaft to a distal end portion of the outer shaft along the longitudinal axis; and a first power drive unit for generating a power, wherein the inner shaft is configured to receive the power so as to result in a rotational motion of the inner shaft, wherein the inner shaft transmits the rotational motion from the proximal side of the outer shaft to the distal end portion of the outer shaft so as to rotate the distal end portion around the longitudinal axis.

2. The rotary self-propelled apparatus according to claim 1, wherein the visualization apparatus having a bending portion, the bending portion having a distal end and a proximal end, the imager being disposed on a distal end of the bending portion, the proximal end of the bending portion being disposed in a distal position to the distal end of the outer shaft and the helical configuration.

3. The rotary self-propelled apparatus according to claim 2, wherein the first power drive unit is disposed on the proximal end side of the outer shaft and the first power drive unit is connected with the torque transmitting member.

4. The rotary self-propelled apparatus according to claim 3, further comprising a second power drive unit disposed on the proximal portion of the outer shaft, the second power drive unit generating a second power such that the power results in a rotation of the outer shaft, the second power drive unit engaging the outer surface of the outer shaft, the rotation of the outer shaft is transmitted from a position engaged by the second power drive unit to the distal end portion of the outer shaft.

5. The rotary self-propelled apparatus according to claim 4, further comprising a control section for controlling the first power drive unit and the second power drive unit so that a rotation number of the inner shaft and a rotation number of a proximal portion of the outer shaft are synchronized with each other.

6. The rotary self-propelled apparatus according to claim 4, further comprising:

a cable inserted through the inner shaft for sending and receiving a signal from the image pickup device.

7. The rotary self-propelled apparatus according to claim 5, wherein the control section is configured such that the second power drive unit receives a control signal generated by the control section, wherein the control signal is configured such that the rotation number of the proximal portion of the outer shaft becomes generally the same as the rotation number of the inner shaft.

* * * * *